United States Patent [19]

Carey et al.

[11] Patent Number: 4,959,358

[45] Date of Patent: * Sep. 25, 1990

[54] DRUG ADMINISTRATION

[75] Inventors: Martin C. Carey, Wellesley; Alan C. Moses, Waban; Jeffrey S. Flier, West Newton, all of Mass.

[73] Assignees: Beth Israel Hospital Assn.; The Brigham and Womens Hospital, Inc., Boston, Mass.

[*] Notice: The portion of the term of this patent subsequent to Oct. 22, 2002 has been disclaimed.

[21] Appl. No.: 197,729

[22] Filed: May 23, 1988

Related U.S. Application Data

[63] Continuation of Ser. No. 614,115, May 25, 1984, Pat. No. 4,746,508, which is a continuation-in-part of Ser. No. 501,187, Jun. 6, 1983, Pat. No. 4,548,922.

[51] Int. Cl.$^5$ ............................................. A61K 31/56
[52] U.S. Cl. ................................... 514/171; 514/37; 514/41; 514/653; 514/946; 514/947
[58] Field of Search ................ 514/171, 653, 946, 947

[56] References Cited

U.S. PATENT DOCUMENTS

| | | | |
|---|---|---|---|
| 3,867,413 | 2/1975 | Von Daehne | 260/347.1 |
| 4,060,606 | 11/1977 | Von Daehne et al. | 514/171 X |
| 4,100,276 | 7/1978 | Von Daehne et al. | 260/397.1 |
| 4,119,717 | 10/1978 | Von Daehne | 424/238 |
| 4,548,922 | 10/1985 | Carey et al. | 516/4 |
| 4,746,508 | 5/1988 | Carey et al. | 424/88 |

OTHER PUBLICATIONS

*Unlisted Drugs*, vol. 28, No. 11, Nov. 1976, p. 190q, "Canaural".
*Unlisted Drugs*, vol. 23, No. 8, Aug. 1971, p. 114j, "Fucitralone".
*Rote Liste*, 1969, p. 488, "Fucidine-H Salbe".

*Primary Examiner*—Leonard Schenkman
*Attorney, Agent, or Firm*—Pennie & Edmonds

[57] ABSTRACT

Compositions and methods useful for the prevention or treatment of a human or animal disorder or for the regulation of the human or animal physiological condition are provided. The compositions used comprise, in admixture, a biologically-effective amount of a drug specific for the disorder or condition and a biocompatible, water-soluble, amphiphilic steroid, other than a natural bile salt, which is capable of increasing drug permeability of the human or animal body surface across which the drug is to be administered, in an amount effective to increase the permeability of the surface to the drug.

19 Claims, No Drawings

DRUG ADMINISTRATION

Part of the work described and claimed herein was supported in part by a grant or award from the United States Government, which has certain rights in the invention.

The application is a continuation of Ser. No. 614,115, 05/25/84, now U.S. Pat. No. 4,746,508 which is a continuation-in-part of application Ser. No. 501,187, filed Jun. 6, 1983, now U.S. Pat. No. 4,548,922 entitled "Drug Administration," which is incorporated herein by reference.

INTRODUCTION

This invention relates to the administration of drugs across human or animal body surfaces. (As used herein, the term "drug" is defined as any biologically-active chemical or natural substance useful for treating a medical or veterinary disorder, preventing a medical or veterinary disorder, or regulating the physiology of a human being or animal). More particularly, the invention relates to an administration method based on the use of biocompatible, water-soluble, amphiphilic steroids capable of increasing the permeability of human and animal body surfaces to a variety of biologically-active substances. Application of admixtures of steroid and drug to mucosal or epithelial surfaces advantageously results in enhanced drug delivery across the body surface.

BACKGROUND OF THE INVENTION

To elicit its characteristic biological response in the body, a drug must be available in an effective concentration at its site of action. The concentration of a drug that reaches its reactive site varies with such factors as the amount of drug administered, the extent and rate of its absorption, distribution, binding or localization in tissues, its biotransformation, and its excretion. (For a review of these topics, see Goodman and Gilman's, *The Pharmacological Basis of Therapeutics*, 6th edition, MacMillan Publishing Co., Inc., New York, 1980, pp. 1-39.) The foregoing factors, and hence the ultimate efficacy of a particular drug, are in turn influenced by the route chosen for drug administration.

The common routes of drug administration are enteral (oral ingestion) and parenteral (intravenous, subcutaneous, and intramuscular) routes of administration. To determine the appropriate mode of drug administration, it is necessary to understand some of the advantages and disadvantages of the route used. For example, intravenous drug administration is advantageous for emergency use when very rapid increases in blood levels are necessary. The intravenous route allows for dosage asjustments when required, and is also useful for administration of large volumes of a drug when diluted. However, there are limitations on the usefulness of intravenous drug administration. One problem is the risk of adverse effects resulting from the rapid accumulation of high concentrations of the drug in plasma and tissues. Consequently, intravenously administered drug solutions must generally be continuously monitored and injected slowly. The intravenous route is not suitable for oily or insoluble substances. Furthermore, intravenous administration is restricted to trained medical personnel.

Other routes of parental administration are often inconvenient or painful for patients especially if frequent administration is required. Subcutaneous injection is used for drugs that are not irritating. This mode of administration is not suitable for delivering large volumes nor is it suitable for administering irritating substances which may cause pain of necrosis at the site of injection. Intramuscular administration is generally suitable for moderate volumes, oily substances, and some irritating substances. The intramuscular route cannot be used during anticoagulant medication and may interfere with the interpretation of certain diagnostic tests.

Oral administration of drugs is generally more convenient and economical and is most acceptable to humans. However, this route of administration requires patient cooperation. Absorption may be inefficient (i.e., incomplete) for poorly soluble, slowly absorbed, or unstable drug preparations, and the time from ingestion to absorption may prohibit effective use in emergency situations. Furthermore, peptides and proteins will often be destroyed by the digestive enzymes, acid, and surface-active lipids in the gut prior to reaching the site of action.

Certain drugs which need to be administered frequently are not effectively absorbed when administered orally and hence must be delivered by injection methods. Yet, a number of problems are associated with conventional injection therapies.

By way of illustration, conventional insulin therapy requires frequent insulin injections resulting in discomfort and disruption of the patient's lifestyle. Hence, many diabetics either refuse insulin therapy altogether or avoid intensive treatment regimens such as those which involve injections with each meal. In addition, certain patients, especially young children, elderly patients, and those who are blind and/or disabled, often have difficulty with insulin self-administration by injection. Furthermore, insulin absorption after subcutaneous injection is variable in terms of rate and amount depending upon factors such as exercise, local blood flow, depth and volume of injection, the presence of local proteases which degrade insulin, and perhaps other, unknown factors. Even presently available short acting and long acting preparations of insulin or mixtures thereof cannot mimic the daily glucose and insulin excursions of non-diabetic individuals. Portable infusion pumps have now been employed to increase the ease of delivering subcutaneously meal-related insulin boluses. However, these devices are externally worn and are therefore cumbersome. They require regular needle replacement, are complicated by local infections at the site of needle placement, are expensive, and are not acceptable to many patients.

It is clear that a reproducible, reliable, and non-invasive means for delivering drugs such as insulin would be highly desirable. What is needed especially in the case of insulin is a delivery system that would permit easy, rapid, and non-invasive administration of insulin at meal times when blood glucose concentration rises to peak levels. Since the discovery of insulin six decades ago, there have been many attempts to develop alternate means of insulin delivery. For instance, insulin has been administered enternally, either alone or encapsulated in liposomes (microcapsules), sublingually, vaginally, and rectally, with and without surfactants.

In addition to the preceding routes of administration, the nasal route has been the subject of investigation for the delivery not only of insulin but of other drugs as well. It is known that certain very small peptides can be absorbed through the nasal mucosa as a "snuff" or directly from aqueous solution without an adjuvant. Examples of peptides which can sometimes be administered by this route are adrenocorticotrophic hormone (ACTH), luteinizing hormone releasing hormone (LHRH), oxytocin and vasopressin. Indeed, for patients with diabetes insipidus, the intranasal route is frequently the means for vasopressin delivery.

In constrast to these directly administrable compounds, many drugs such as insulin are inefficiently absorbed across mucous membranes at physiological pH in the absence of adjuvants. Several workers have attempted to mix insulin with adjuvants that might enhance nasal insulin absorption. Hirai et al., Int. J. Pharmaceutics (1981) 9:165–184; Hirai et al., Diabetes (1978) 27:296–299; British Pat. No. 1,527,605; and U.S. Pat. No. 4,153,689; and Pontiroli et al. (1982) Br. Med J. 284:303–386, have described the use of various bile salts to enhance absorption of insulin by the nasal mucosa While the nasal mucosal route has received considerable attention for systemic drug delivery, it has also hitherto been known that drugs may be applied to mucous membranes of the conjunctiva, nasopharynx, oropharynx, ear canal, respiratory tract, vagina, rectum, colon, and urinary bladder for their local effects.

SUMMARY OF THE INVENTION

We have discovered an effective means of administering a drug to a human being or animal which avoids many of the problems associated with other modes of administration such as injection. The invention provides methods and compositions useful for the prevention and/or treatment of human or animal disorders and for the regulation of aspects of human or animal physiology, e.g., fertility. The compositions employed are admixtures comprising: (a) as active ingredient, a drug specific for a given disorder or condition in a biologically-effective amount; and (b) as adjuvant, a biocompatible, water-soluble, amphiphilic steroid, other than a natural bile salt, capable of increasing drug permeability of a human or animal body surface across which the drug is to be administered, in an amount effective to increase the permeability of said surface to said drug. The admixtures can be applied advantageously to such body surfaces as mucosal and epithelial surfaces to achieve improved drug transport across the surfaces, thereby enhancing the delivery of the drug to its ultimate site of action in the body.

Preferably the steroid adjuvant is one of the naturally occurring steroids, fusidic acid or cephalosporin $P_1$, $P_2$, $P_3$, $P_4$ or $P_5$ or a derivative of any of these. The steroid may have the following formula:

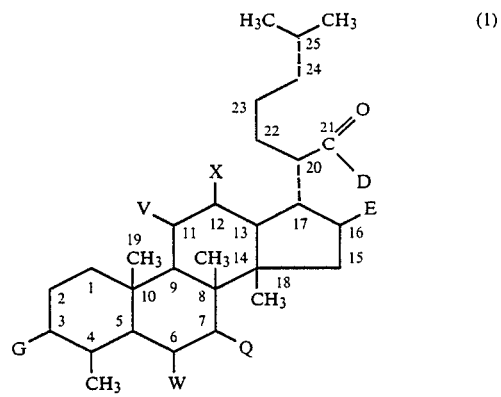

wherein each dashed line, independently, represents a single or a double bond; D is a group which renders an effective amount of the steroid water soluble within the range of about pH 2 to about pH 12; E and G are individually OAc, OH, or a lower alkyl or lower heteroalkyl; W is OAc or H; and Q, V and X are individually OH or H. Most preferably the steroids of formula (1) have functional groups as follows: E is $\beta$ OAc, $\alpha$ OH, or a lower (3 or fewer carbons) alkyl or heteroalkyl group in $\beta$ position; G is $\alpha$ OAc, OH, lower alkyl, or lower heteroalkyl; W is $\alpha$ OAc or H; Q is OH or H, provided that, when W is $\alpha$ OAc and Q is $\alpha$ OH, Q must be $\alpha$-axial; V is H or $\alpha$ OH; and X is H or $\alpha$ OH; provided that the steroid contains two or three polar functions exclusive of D. Three OH groups are allowed provided that one is $C_{16}$ $\alpha$-axial, replacing OAc at that position. (As used herein, the symbol "OAc" refers to the acetoxyl radical $OCOCH_3$.)

The steroid of formula (1) can be unconjugated, i.e., D is $O^-Na^+$, $O^-K^+$, $O^-Rb^+$, $O^-Cs^+$, or some other ionic configuration, or it can be conjugated, i.e., D is an organic group containing at least one carbon atom. Preferably group D has a molecular weight below about 600 daltons and is one of the following groups:

(a) a peptide of one, two, or three amino acids and containing an ionic function which is dissociated within the range of about pH 2 to about pH 12;

(b) a heteroalkyl group of about three or fewer carbon atoms which contains an ionic function which is dissociated within the range of about pH 2 to about pH 12;

(c) a uronic acid of about six or fewer carbon atoms which contains an ionic function which is dissociated within the range of about pH 2 to about pH 12;

(d) a polyether containing between about six and about fourteen carbon atoms, inclusive, which terminates in an ionic function which is dissociated within the range of about pH 2 to about pH 12; or (e) a polyether containing between about sixteen and about twenty-four carbon atoms, inclusive, and optionally terminating in an ionic function which is dissociated within the range of about pH 2 to about pH 12.

Group D is preferably bonded to $C_{21}$ via an amide or ester linkage.

Preferably the steroid used in the invention is characterized in that the unconjugated derivative of the steroid is retained on hydrophobic column for a length of time sufficient to produce a k' factor value of at least about 4, the k' factor value being obtained by subjecing a monomeric solution of 1 mg/ml of such steroid derivative to high-performance liquid column chromatography at 3,000 psi, using a 250×4.6 mm column having octadecylsilane-coated 5 μm silica particles as the stationary phase and a mobile phase, delivered at 1.0 ml/min., consisting of 75% methanol in water, v/v, buffered with 0.005 M $KH_2PO_4/H_3PO_4$ to give an apparent pH value, as measured using a glass electrode, of 5.0, the k' factor value being defined by $k'=(t_r-t_0)/t_0$, where $t_0$ is the retention time in the column of the solvent front and $t_r$ is the retention time in the column of the steroid derivative as measured by obtaining the elution profile of the steroid derivative by absorbance at 210 nm.

Preferably the steroid is further characterized in that the critical micellar temperature (CMT) (the temperature at which the steroid ceases to be an insoluble crystal or gel and begins to go into solution and self-associate in solution) of an aqueous 1% solution, w/v, of the steroid is below human or animal body temperature, and optimally below about 0° C. within the range of about pH 2 to about pH 12 (a measure of solubility); and the critical micellar concentration (CMC) (the concentration at which the steroid ceases to be an ideal solution and begins to self-associate) is as high as 8 mMolar but preferably less than 4 mM and more preferably less than 2 mMolar at 37° C. in 0.15 M NaCl as measured by surface tension.

Preferred steroids are ionized or partially ionized alkali salts of fusidic acid, 24,25-dihydrofusidic acid, cephalosporin $P_1$ and $C_{21}$ conjugates of these; and tauro-24,25-dihydrofusidate and glyco-24,25-dihydrofusidate. Other preferred steroids may be 17,20-24,25-tetrahydrofusidic acid, 3-acetoxyl-fusidic acid, cephalosporin $P_2$-$P_5$, and $C_{21}$ conjugates of these; and tauro-17,20-24,25-tetrahydrofusidate, tauro-16α-OH-24,25-dihydrofusidate, tauro-16α-OH-17,20-24,25-tetrahydrofusidate, tauro-16-O-methyl-ether-24,25-dihydrofusidate, tauro-16-O-methyl-ether-17,20-24,25-tetrahydrofusidate. The foregoing preferred steroids must be freely soluble in water at the pH of the composition to be administered. A broad spectrum of drugs may be used including but not limited to (a) peptides and polypeptides which have a molecular weight between about 100 and about 300,000 daltons, (b) non-peptides, and (c) other drugs.

The invention permits more effective, safer and convenient administration across a body surface of a human being or animal, e.g., any mucosal surface, including but not limited to oropharynx, ear canal, respiratory tract, nasopharynx, conjunctiva, rectal, gastric, intestinal, endometrial, cervical, vaginal, colon, urethra, urinary bladder, and tympanic membrane, of a wide range of drugs, some of which normally cannot be so administered. For example, in contrast to intravenous injection, the invention allows for convenient patient self-administration of drugs, making it more likely that the patient will adhere to prescribed treatment schedules. The invention will deliver drugs more quickly than oral, subcutaneous, or intramuscular administration and is potentially more effective in delivering drugs to a localized site than is intravenous administration. In contrast to oral administration, drugs administered by the method of the present invention do not need to pass through the liver where they might be metabolized in order to reach the site of action, in some cases reducing liver toxicity. Because drugs can be delivered more efficiently to the site of action or into the blood stream, in many cases a higher percentage of a given drug will reach the site than when administered by other means, thereby reducing the quantity of the drug that needs to be administered. Administration of reduced, quantities of drug can be more cost effective than administration of the same drug by a conventional method. Alternatively, this method provides a means for delivering increased amounts of drug to a site, if desired or necessary. In addition, administration, according to the present invention, does not have deleterious toxic side effects. In particular, the steroids of the invention are able to potentiate the transport and enhance absorption of drugs across mucosal surfaces into the circulation while causing less irritation, burning sensation or other local toxicity than is a characteristic by-product of transport facilitaion by other carrier molecules.

The invention also allows drug administration to be tailored much more closely to cyclic disease states than is possible with other forms of administration. This is of particular importance with diseases (such as diabetes) in which drug requirements vary during the course of a day.

It is contemplated that the adjuvants and methods of the instant invention can be used to administer agents useful for vaccination (both active immunization with antigens and immunogenic fragments thereof as well as passive immunization with antibodies and neutralizing fragments thereof) and to administer agents useful for birth control.

It is further contemplated that the adjuvants and methods of the instant invention may potentially be useful for the delivery across plant surfaces of antiviral agents, systemic insecticides and herbicides; and across arthropod surface of contact insecticides and miticides.

Other features and advantages of the invention will be apparent from the following description of the preferred embodiments thereof, and from the claims.

DESCRIPTION OF THE INVENTION

The steroid which is admixed with a drug to be administered is preferably an ionized or partially ionized, water-soluble derivative of fusidic acid or cephalosporin $P_1$-$P_5$, preferably a derivative having formula (1), above. These steroid molecules are all characterized in that they have the specific four-ring structure of fusidic acid and cephalosporin $P_1$-$P_5$, including the boat conformation of the B ring (in contrast to cholesterol derivatives such as bile salts, which have the B ring in the lower energy, more stable chair conformation).

The structure of the steroid molecule affects its chemical properties and thus its functioning as a drug transporting molecule. We believe that all of the steroid molecules used in the invention facilitate transport by self-associating to form reversed micelles within the membrane across which the drug is being transported; these reversed micelles, it is believed, function as pores, allowing the drug to pass through. A measure of a given steroid molecule's ability to form such reversed micelles is the hydrophobicity of the unconjugated form of the molecule, a property which can be quantified using the k' factor value, which is computed by observing the steroid's retention time in a high-performance liquid chromatography (HPLC) column under the conditions described above. As mentioned above, the k' value of the unconjugated derivative of the steroid should be at least about 4 for the steroid to be suitable in the therapeutic compositions of the invention.

Critical micellar temperature (CMT) is an additional measure of a steroid's utility in the compositions of the invention. CMT is the temperature at which the steroid molecules abruptly become soluble and self-associate into micelles from the gel or crystalline state. This change is a reflection of the colligative properties of the system, and the micelles formed at a temperature just above the CMT can be small, e.g. dimers. The steroid molecules used in the invention should have a great enough tendency to self-associate to give a CMT at or below human or animal body temperature and optimally below about 0° C., for a 1% aqueous solution, w/v, within the range of about pH 2 to about pH 12.

The steroids of formula (1) can be conjugated or unconjugated at $C_{21}$. The conjugating group can be any organic group which does not raise the critical micellar temperature of a 1% solution of the steroid above human or animal body temperature and preferably does not raise the CMT above about 0° C. within the range of about pH 2 to about pH 12 and does not raise the CMC above about 8 mMolar at 37° C. in 0.15 M NaCl as measured by surface tension. Preferably, the CMC is less than 2 mMolar under similar conditions.

The conjugating group can be, e.g., any ionic function-containing straight or branch-chained amino acid. The amino acid can be aliphatic or aromatic, and can also be a homo- or a dihomo-amino acid, e.g. homotaurine or homoglycine, or an amphoteric amino acid, e.g., sulfobetaine or phosphobetaine. A straight or branched chain di- or tripeptide which terminates in an ionic functiom which is dissociated within the range of about pH 2 to about pH 12 can also be employed. Peptides larger than tripeptides generally should not be used because they can lead to unacceptably lower solubility. Any suitable uronic acid, e.g. glucuronic acid, can also be used.

Preferred conjugating amino acids are glycine and taurine. Preferred straight-chain peptides are diglycine and glutathione, and preferred branched chain peptides are sarcosylcysteine, hydroxyprolinetaurine, and sarcosyltaurine.

When the conjugating group is a polyether of at least sixteen carbon atoms, the group need not (although it may) contain an ionic function; the ionic function is unnecessary because such groups are highly polar and thus confer solubility without ionization. For smaller polyether groups, an ionic function is generally necessary, although it can be weakly ionizable since the smaller polyethers are polar themselves.

The group bonded to each of $C_6$ and $C_{16}$, independently, (W and E in formula (1)) can be OAc (OCOCH$_3$) as in naturally occurring fusidic acid and cephalosporin P$_1$. Alternatively, E can be OH, an alkyl (e.g., methyl or ethyl) or a different heteroalkyl (e.g. alkyloxy, alkylthio, or ether derivative) group of three or fewer carbon atoms; larger groups can unacceptably lower solublity. Group G, bonded to $C_3$, can be OH, as in naturally occurring fusidic acid and cephalosporin $P_1-P_5$. G can also be OAc, a lower alkyl group, or a different lower heteroalkyl group. Group W, if OAc, preferably should be in the β-axial orientation.

The molecule should possess two or three polar functions, exclusive of any side chain at $C_{21}$, at the positions indicated above where acetoxyl and hydroxyl groups can be located.

The k' and CMT of the steroids used in the compositions of the invention are influenced by whether the steroid is conjugated at $C_{21}$ and, if so, by the nature of the conjugating group. Additionally, a polar group at position 16 is essential for solubility (See position E on formula 1). Because the k' factor value is influenced by the polarity of any conjugating group, unconjugated derivatives must be used in numerical comparisons involving steroids which are conjugated with different groups, or comparisons involving both conjugated and unconjugated steroid. Overall hydrophobicity and k' factor value generally decrease as the polarity of the conjugating group increases. However, such decrease is not a reflection of the hydrophobicity of the steroid nucleus. It is this hydrophobicity which is the important parameter for purposes of reversed micelle formation.

As discussed supra, the k' factor value of the unconjugated derivative of any such steroid should be at least about 4. For example some k' values of some unconjugated steroids useful in the invention are: cephalosporin $P_1$ (k'=9.5); fusidic acid (k'=20.7); 3-acetoxyl-fusidic acid (k'=26.4); 24,25-dihydrofusidic acid (k'=27.1). To give a few minimum k' values of conjugated steroids, the k' factor value of a glycine-conjugated steroid should be at least about 2 to be useful in the invention. For a taurine-conjugated steroid, the k' factor value should be at least about 1.

It is desirable that conjugated steroids have strongly ionized conjugating groups which are capable of forming micelles at low pH and concentrations (the critical micellar concentration, CMC, is a measure of this latter property). As mentioned above, examples of such desirable conjugating groups include but are not limited to taurine, homotaurine, sarcosyltaurine, and sulfobetaine. Steroids conjugated with such groups also have the advantages of stability and ease of synthesis.

Conjugation has additional effects as well, which provide the opportunity to tailor the conjugated steroid to a given clinical situation. For example, if the steroid is to be used to transport a drug across a mucosal membrane, e.g. the nasal mucosa, relatively long (e.g. homotaurine), branched (e.g. sarcosyltaurine), bulky (e.g. glucuronic acid), and amphoteric (e.g. sulfobetaine) groups are desirable, since they may cause the steroid to be held in the nasal membrane somewhat longer than unconjugated steroids or steroids conjugated with smaller conjugating groups.

Conjugation also, in some instances, lowers the CMC, so that only a small amount of steroid need be used. Strong acidic conjugating groups render the steroid resistant to being taken out of solution by variations in pH, ionic strength, and by the presence of other ions (e.g. Ca$^{++}$) and other macromolecules. Conjugation further prevents retention by the body, promotes rapid excretion, and prevents hepatic metabolism to potentially toxic metabolites (Beauaboin et al., J. Clin. Invest. (1975) 56:1431-1441).

As mentioned above, conjugating groups are bonded to $C_{21}$ via any suitable linkage, e.g. amide or ester. Conjugation is carried out using conventional techniques. As an example, taurine bonded to $C_{21}$ via an amide linkage is shown below (the presence of a cation, e.g. K$^+$ or Na$^+$, is indicated in the parentheses):

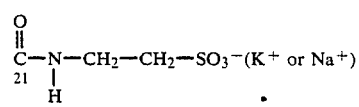

The properties of the steroid are also affected by the nature of the substituents at $C_3$, $C_6$ and $C_{16}$. Generally, OAc groups at these positions tend to aid solubility;

however, OAc groups are also quite labile, and tend to decrease stability and shelf-life.

The fusidic acid or cephalosporin $P_1$-$P_5$ derivatives can be made by appropriately modifying commercially available fusidic acid or cephalosporin $P_1$-$P_5$. Such techniques are known in the art.

The drugs which are admixed with a steroid carrier preferably have a molecular weight of between about 100 daltons and about 300,000 daltons. The drug may be either water soluble or lipid soluble, and may be a peptide, e.g. a peptide hormone such as insulin or a peptide hormone precursor such as proinsulin. Water soluble drugs, e.g. some peptides and vitamins, can also be transported across mucosal membranes by any of the steroids of the invention, including those whose unconjugated derivatives have relatively low k' values (between about 7 and about 15). For hydrophobic, lipid-soluble drugs, e.g. the lipid-soluble vitamins, the unconjugated derivative of the steroid should have a higher k' value, preferably above about 20.

Drugs for which the method of administration of the invention is particularly important are peptides. Suitable peptides include but are not limited to insulin, proinsulin, glucagon, parathyroid hormone and antagonists of it, calcitonin, vasopressin, renin, prolactin, growth hormone, thyroid stimulating hormone, corticotropin, follicle stimulating hormone, luteinizing hormone, chorionic gonadotropin, atrial peptides (a natriuretic factor), interferon, tissue plasminogen activator, gamma-globulin, Factor VIII, and chemical modifications of these peptides.

The invention can also be used to administer hormone releasing hormones, e.g. growth hormone releasing hormone, corticotropin releasing factor, luteinizing hormone releasing hormone, growth hormone release inhibiting hormone (somatostatin) and thyrotropin releasing hormone.

Other suitable drugs include the physiologically active enzymes: transferases, hydrolases, isomerases, proteases, ligases, and oxidoreductases such as esterases, phosphatases, glycosidases and peptidases; enzyme inhibitors such as leupeptin, chymostatin and pepstatin; and growth factors such as tumor angiogenesis factor, epidermal growth factor, nerve growth factor and insulin-like growth factors. Other suitable drugs are those normally absorbed to a limited extent across the gastrointestinal mucosa after oral administration; e.g. antihistamines (e.g. diphenhydramine and chlorpheniramine), and drugs affecting the cardiovascular (e.g., antihypertensives), renal, hepatic and immune systems (including vaccines). Additionally, sympathomimetic drugs, such as the catecholamines (e.g. epinephrine) and non-catecholamines (e.g. phenylephrine and pseudoephedrine) may be administered according to the method of the present invention.

Drugs such as anti-infective agents, including antibacterial, antiviral and antifungal agents may also be administered according to the method of the present invention. For example, antibiotics such as the aminoglycosides (e.g., streptomycin, gentamicin, kanamycin etc.) are generally not adequately absorbed after oral administration, and may therefore be advantageously administered by the method of the invention.

Many other drugs may also be administered according to the invention, e.g. the many drugs currently used to treat arthritis such as narcotic pain relievers. Anti-inflammatory agents (e.g. indomethacin, dexamethasone and triamcinolone), anti-tumor agents (e.g. 5-fluorouracil and methotrexate) and tranquilizers such as diazepam may also be administered according to the invention.

Other suitable drugs are the water insoluble, fat-soluble hydrophobic drugs, e.g. steroids such as progesterone, estrogens (including contraceptives such as ethinyl estradiol) and androgens and their analogs, and the fat-soluble vitamins, e.g. vitamins A, D, E and K, and their analogs.

The surface across which transport occurs may be any mucosal surface such as the nasopharynx, conjunctiva, oropharynx, ear canal, rectal, intestinal (enteral), respiratory tract, endometrial, cervical vaginal, urethra, urinary bladder or, in some circumstances, a skin surface such as the axilla, the gluteal cleft, tympanic membrane, between the toes, and the groin. Additionally, transport of the drug according to the method of the present invention may enhance penetration into the skin for increased local effects.

The ratio of drug and steroid present in a therapeutic composition will vary depending on a number of factors, including the k' and CMC of the steroid, the dosage of the drug to be administered, and the chemical characteristics, e.g. hydrophobicity, of the drug. Generally, the steroid is provided in an aqueous physiological buffer solution which is then mixed with the drug. The solution generally contains about 0.1% to about 2.5%, w/v, steroid in a physiologically acceptable carrier, e.g. sodium phosphate buffered NaCl, pH 5-8, having a NaCl concentration of about 0.05M to about 0.6M.

The concentration of the drug in the solution will of course vary widely, depending on the nature of the drug, and on the extent to which absorption is facilitated by the steroid. In some cases, administration according to the invention will enable the delivery of a higher dosage of the drug where needed than if the conventional mode of administration is used; in other cases, a much smaller dosage can be used because of efficient administration to a site. For instance, the amount of drug potentially can be decreased to one thousandth the amount or increased to ten times the amount of the drug normally used with conventional administration methods.

The therapeutic composition may contain, in addition to steroid and drug, any other desired non-toxic, pharmaceutically acceptable substances, e.g. a preservative such a phenol or cresol or stabilizing agents.

The dosage given at any one time will depend on a number of factors including, in addition to those mentioned above, the frequency of administration.

The compositions of the present invention may be administered to human and animal body surfaces in a variety of forms, including but not limited to, sprays, drops, suppositories, douches, salves, ointments, and creams. Some compositions may be advantageously applied in long term release dosage forms such as slow release, continuous release and intermittent release dosage forms. These long term release dosage forms include but are not limited to polymers, microcapsules, microspheres, osmotic diffusion devices and membrane release devices.

EXAMPLES

The following examples are intended to illustrate the invention, without acting as a limitation upon its scope.

Examples 1-14 demonstrate the effectiveness of using various fusidic acid derivatives (Leo Pharmaceuticals, Ballerup, Denmark) and cephalosporin as adjuvants for the delivery of insulin, glucagon, human chorionic gonadotropin (hCG), proinsulin, corticotropin releasing-factor (CRF) and epinephrine across nasal mucosal membranes or conjunctival membranes in humans or sheep. Assays of insulin, glucagon, and hCG across nasal mucosal membranes and conjunctival membranes were accomplished by highly specific radioimmunoassay (RIA). (Protocols for RIA of insulin followed the procedures given in "GammaCoat [$^{125}$I] Insulin Radioimmunoassay Kit," Cat. No. CA-532, Clinical Assays Division of Travenol Laboratories, Inc., Cambridge, Mass. and for glucagon, the procedures given in "Protocol for the Radioimmunoassay of Glucagon [$^{125}$I]," Cat. No. 520, Cambridge Medical Diagnostics, Middle Billerica, Mass.) In the case of proinsulin, an insulin immunoassay with significant cross-reactivity for proinsulin was adapted to estimate the amounts of proinsulin absorbed. (The protocol is given in "Insulin [$^{125}$I] Radioimmunoassay," Corning Medical and Scientific, Medfield, Mass.) The values obtained for insulin were adjusted to correlate with known cross-reactivity (i.e., 36%) of proinsulin in the assay. The "GammaDab [$^{125}$I] β-HCG Radioimmunoassay Kit," Clinical Assays Cat. No. 589, Clinical Assays Division of Travenol Laboratories, Inc., Cambridge, Mass. was used to evaluate hCG levels in serum.

INTRANASAL ADMINISTRATION OF INSULIN TO HUMANS

Example 1

The final concentration of insulin varied for each subject since they were of different weights.

Sodium tauro-24,25-dihydrofusidate was dissolved in 0.15M NaCl, pH 7.4 to form a 5% solution, w/v. Commercially available porcine regular insulin (U-500) (Eli Lilly & Co., Indianapolis, Ind.) was mixed in a total volume of 2.0 ml with 0.15M NaCl, pH 7.4 and the 5% solution of sodium tauro-24,25-dihydrofusidate to give final concentrations of 216 U/ml insulin and 1% (w/v) sodium tauro-24,25-dihydrofusidate. A normal human subject (subject 40) was administered at time 0, by nasal spray, two 75 microliter aliquots, so that the dosage of insulin administered to the subject was 0.5 Units/kg body weight.

For subjects 92 and 93, sodium tauro-24,25-dihydrofusidate was dissolved in 0.15M NaCl, 0.05M sodium phosphate buffer, pH 7.6 to form a 2% solution, w/v. Insulin was mixed in a total volume of 7.0 ml with the 0.15M NaCl, 0.05M sodium phosphate buffer and the 2% solution of sodium tauro-24,25-dihydrofusidate to give final concentrations of 220 Units/ml for subject 92 and 233 Units/ml for subject 93.

As shown in Table I, below, five minutes after nasal administration, subject 40's serum insulin level had increased more than twenty-fold, demonstrating that the insulin had been rapidly and effectively absorbed across the nasal mucosa. After ten minutes serum insulin levels for subjects 92 and 93 had increased more than ten-fold, indicating rapid absorption across the nasal mucosa. Furthermore, as is shown in Table I, each subjects' blood glucose was lowered significantly after twenty minutes, and was reduced more than fifty percent after thirty minutes for subjects 40 and 92.

TABLE I
STUDY OF NASALLY ADMINISTERED INSULIN IN SODIUM TAURO-24,25-DIHYDROFUSIDATE TO HUMANS

| | Time (minutes) | Blood Glucose (mg/dl) | Serum Insulin (μU/ml) | Insulin (μU/ml above basal) |
|---|---|---|---|---|
| SUBJECT 40 | −20 | 89.9 | 5.6 | 1.1 |
| | −10 | 88 | | |
| | 0 | 89 | 4.5 | 0 |
| | +5 | | 115 | 110.5 |
| | 10 | 82 | 100 | 95.5 |
| | 15 | | 95 | 90.5 |
| | 20 | 54.5 | 62 | 57.5 |
| | 25 | | 30 | |
| | 30 | 31.5 | 22 | 17.5 |
| | 40 | 37.5 | 10 | 5.5 |
| | 50 | 50 | 6.4 | 1.9 |
| | 60 | 72 | 8.8 | 4.3 |
| | 75 | 85 | 5 | |
| | 90 | 89 | 3.5 | |
| SUBJECT 92 | −20 | 81 | 5.0 | .3 |
| | 0 | 80 | 4.7 | 0 |
| | +5 | 79.5 | 52 | 47.3 |
| | 10 | 74.5 | 68 | 63.3 |
| | 15 | 61.5 | 55 | 50.3 |
| | 20 | 47 | 35 | 30.3 |
| | 30 | 34.5 | | |
| | 40 | 53.5 | 6.4 | 1.7 |
| | 50 | 67 | 3.2 | 0 |
| | 60 | 71.5 | 2.8 | 0 |
| SUBJECT 93 | −20 | 91.5 | 7.2 | 1.8 |
| | 0 | 89 | 5.4 | 0 |
| | +5 | 89.5 | 54 | 48.6 |
| | 10 | 85 | 58 | 52.6 |
| | 15 | 75.5 | 28.5 | 23.1 |
| | 20 | 66 | 19.5 | 14.1 |
| | 30 | 65.5 | 7.2 | 1.8 |
| | 40 | 75 | 4.7 | 0 |
| | 50 | 84.5 | 9.4 | 4.0 |
| | 60 | 84.5 | 6.2 | 0.8 |

Example 2

Unconjugated sodium fusidate was dissolved in 0.15M NaCl, pH 7.4 to form a 3% solution w/v. Commercially available insulin (U-500) was mixed in a total volume of 3 ml with 0.15M NaCl, pH 7.4 and the 3% solution of sodium fusidate to give final concentrations of 210 Units/ml insulin and 1% (w/v) sodium fusidate. A normal human subject was administered the insulin preparation by nasal spray at time 0 as described in Example 1. The results obtained are shown in Table II below. Twenty minutes after nasal administration the subject's serum insulin level had increased more than fifteen-fold. Additionally, as is shown in Table II, the subject's blood glucose was reduced more than fifty percent after thirty minutes.

TABLE II
STUDY OF NASALLY ADMINISTERED INSULIN IN UNCONJUGATED SODIUM FUSIDATE, pH 7.4 TO HUMANS

| | Time (minutes) | Blood Glucose (mg/dl) | Serum Insulin (μU/ml) | Insulin (μU/ml above basal) |
|---|---|---|---|---|
| SUBJECT 33 | −20 | 75.5 | 3.7 | −.8 |
| | 0 | 79 | 4.5 | 0 |
| | +5 | | 16 | 11.5 |
| | 10 | 77 | 60 | 55.5 |
| | 15 | | 80 | 75.5 |
| | 20 | 59.5 | 85 | 80.5 |
| | 30 | 34 | 28 | 23.5 |
| | 40 | 43.5 | 10.5 | 6 |
| | 50 | 56.5 | 7 | 2.5 |
| | 60 | 68.5 | 4.5 | 0 |

Example 3

The insulin preparation was obtained by the same procedure as described in Example 2. However, the pH of the solution was adjusted to pH 7.95 and the final insulin concentration was 267 Units/ml. A normal human subject was administered the insulin preparation by nasal spray at time 0 as described in Example 1. As shown in Table III below the subject's serum insulin level had increased more than thirty-five fold after fifteen minutes. Furthermore the patient's blood glucose was lowered significantly after thirty minutes.

TABLE III
STUDY OF NASALLY ADMINISTERED INSULIN IN UNCONJUGATED SODIUM FUSIDATE, pH 7.95 TO HUMANS

| | Time (minutes) | Blood Glucose (mg/dl) | Serum Insulin ($\mu$U/ml) | Insulin ($\mu$U/ml above basal) |
|---|---|---|---|---|
| SUBJECT 35 | −20 | | 1.7 | 0 |
| | 0 | 80 | 1.7 | 0 |
| | +5 | | 45 | 43.3 |
| | 10 | 80 | 60 | 58.3 |
| | 15 | | 34 | 32.3 |
| | 20 | 64 | 20 | 18.3 |
| | 30 | 46 | 10 | 8.3 |
| | 40 | 56 | 4.5 | 2.8 |
| | 50 | 73.5 | 14 | 12.3 |
| | 60 | 84 | 7 | 5.3 |

Example 4

Sodium glyco-24,25-dihydrofusidate was dissolved in 0.15M NaCl, pH 7.6 to form a 3% solution w/v. Commercially available porcine insulin (U-500) was mixed in a total volume of 3.0 ml with 0.15M NaCl, pH 7.6 and the 3% solution of sodium glyco-24,25-dihydrofusidate to give final concentrations of 216 Units/ml insulin and 1% (w/v) sodium glyco-24,25-dihydrofusidate. Subject 40 was administered the insulin preparation by nasal spray at time 0 as described in Example 1. As shown in Table IV below, five minutes after nasal administration, subject 40's serum insulin had increased more than twenty-fold, indicating that the insulin had been rapidly and effectively absorbed through the nasal mucosa. Furthermore, the subject's blood glucose was lowered significantly after twenty minutes.

TABLE IV
STUDY OF NASALLY ADMINISTERED INSULIN IN SODIUM GLYCO-24,25-DIHYDROFUSIDATE TO HUMANS

| | Time (minutes) | Blood Glucose (mg/dl) | Serum Insulin ($\mu$U/ml) | Insulin ($\mu$U/ml above basal) |
|---|---|---|---|---|
| SUBJECT 40 | −20 | 90 | 3.5 | .8 |
| | 0 | 86.5 | 2.7 | 0 |
| | +5 | | 66 | 63.3 |
| | 10 | 81 | 58 | 55.3 |
| | 15 | | 38 | 35.3 |
| | 20 | 60 | 23 | 20.3 |
| | 30 | 51 | 6 | 3.3 |
| | 40 | 67.5 | 4.5 | 1.8 |
| | 50 | 78.5 | 5.6 | 2.9 |
| | 60 | 82.5 | 2.4 | −.3 |

Example 5

For subject 34, sodium 24,25-dihydrofusidate was dissolved in 0.15M NaCl, pH 8.1 to form a 3% solution w/v. Commercially available porcine insulin (U-500) was mixed in a total volume of 3 ml with 0.15M NaCl, pH 8.1, and the 3% solution of sodium 24,25-dihydrofusidate to give final concentrations of 190 Units/ml insulin and 1% (w/v) sodium 24,25-dihydrofusidate. For subject 35, the insulin preparation was made in the same manner as described above except that the initial sodium 24,25-dihydrofusidate concentration was 3.75% (w/v) and the final insulin concentration was 267 Units/ml. The two normal human subjects were administered the insulin preparation by nasal spray at time 0 as described in Example 1. As shown in Table V below, fifteen minutes after nasal administration subject 34's serum insulin level had increased thirty-fold and the subject's blood glucose was lowered significantly after thirty minutes. Subject 35 showed a dramatic increase in serum insulin (63.5-fold) after ten minutes, demonstrating that the insulin had been rapidly and effectively absorbed through the nasal mucosa. Additionally, the subjects' blood glucose was lowered more than fifty percent after thirty minutes.

TABLE V
STUDY OF NASALLY ADMINISTERED INSULIN IN SODIUM 24,25-DIHYDROFUSIDATE TO HUMANS

| | Time (minutes) | Blood Glucose (mg/dl) | Serum Insulin ($\mu$U/ml) | Insulin ($\mu$U/ml above basal) |
|---|---|---|---|---|
| SUBJECT 34 | −20 | 76 | 2.2 | .3 |
| | 0 | 76.5 | 1.9 | 0 |
| | +5 | | 9.6 | 7.7 |
| | 10 | 79 | 36 | 34.1 |
| | 15 | | 38 | 36.1 |
| | 20 | 65.5 | 28 | 26.1 |
| | 30 | 49 | 9.6 | 7.7 |
| | 40 | 44.5 | 7 | 5.1 |
| | 50 | 52.5 | 3 | 1.1 |
| | 60 | 69 | 2 | 1 |
| SUBJECT 35 | −20 | 75.5 | 1.6 | −1 |
| | 0 | 76.5 | 2.6 | 0 |
| | +5 | | 94 | 91.4 |
| | 10 | 72 | 165 | 162.4 |
| | 15 | | 130 | 127.4 |
| | 20 | 42.5 | 98 | 95.4 |
| | 30 | 21.5 | 37 | 34.4 |
| | 40 | 29 | 8.4 | 5.8 |
| | 50 | 44 | 6.4 | 3.8 |
| | 60 | 54.5 | 3.5 | .9 |

Example 6

Cephalosporin $P_1$ was dissolved in 0.15M NaCl, pH 7.6 to form a 5% solution, w/v. Commercially available insulin was mixed with 0.15M NaCl, pH 7.6 and the 5% solution of cephalosporin $P_1$ to give final concentrations of 220 Units/ml insulin and 1% (w/v) cephalosporin $P_1$. A human subject was administered, by nasal spray two 75 microliter aliquots (33 Units) at time 0 so that the dosage of insulin administered to the subject was 0.5 Units/kg body weight.

As shown in Table VI, the subject's blood glucose level decreased slightly. Serum insulin levels are not yet available.

TABLE VI
STUDY OF NASALLY ADMINISTERED INSULIN - IN CEPHALOSPORIN $P_1$ TO HUMANS

| Time (minutes) | Blood Glucose (mg/dl) |
|---|---|
| −15 | 96 |
| 0 | 97.5 |
| +5 | 92 |
| 10 | 91 |
| 15 | 90.5 |
| 20 | 86.5 |

TABLE VI-continued

STUDY OF NASALLY ADMINISTERED INSULIN IN CEPHALOSPORIN P₁ TO HUMANS

| Time (minutes) | Blood Glucose (mg/dl) |
|---|---|
| 30 | 76.5 |
| 45 | 82.5 |
| 60 | 88.5 |

CONJUNCTIVAL ADMINISTRATION OF INSULIN TO SHEEP

Example 7

Sodium tauro-24,25-dihydrofusidate was dissolved in 0.15M NaCl, 0.05M sodium phosphate buffer, pH 7.6 to form a 2% solution, w/v. Porcine insulin (U-500) was mixed in a total volume of 1 ml with 0.15M NaCl, 0.05M sodium phosphate buffer, pH 7.6 and the 2% solution of sodium tauro-24,25-dihydrofusidate to give final concentrations of 97.5 Units/ml insulin and 1% (w/v) sodium tauro-24,25-dihydrofusidate. Two sheep were administered 350 mg ketamine (a general anesthetic) intravenously and 1.0 Unit/kg body weight of insulin to the conjunctival sac as drops at time 0. As shown in Table VII below, five minutes after conjunctival administration, the serum insulin level of both sheep had increased greater than five fold. Unlike human subjects, sheep do not respond to these increments in serum insulin levels with a decrease in blood glucose concentrations.

TABLE VII

STUDY OF CONJUNCTIVAL ADMINISTRATION OF INSULIN IN SODIUM TAURO-24,25-DIHYDROFUSIDATE TO SHEEP

|  | Time (minutes) | Serum Insulin (μU/ml) |
|---|---|---|
| Sheep A | −15 | 24 |
|  | −5 | |
|  | 30 | |
|  | 0 | 24.5 |
|  | +5 | >200 |
|  | 10 | >200 |
|  | 15 | >200 |
|  | 20 | 190 |
|  | 30 | >200 |
|  | 45 | 195 |
|  | 60 | 125 |
|  | 75 | 70 |
|  | 90 | 180 |
| Sheep B | −15 | 22 |
|  | −5 | 22 |
|  | 0 | 42 |
|  | +5 | >200 |
|  | 10 | >200 |
|  | 15 | 49 |
|  | 20 | 35 |
|  | 30 | 58 |
|  | 45 | 160 |
|  | 60 | 82 |

INTRANASAL ADMINISTRATION OF GLUCAGON TO SHEEP

Example 8

Sodium tauro-24,25-dihydrofusidate was dissolved in 0.15M NaCl, 0.5M sodium phosphate, pH 7.6. The dry powder of bovine glucagon (Eli Lilly & Co., Indianapolis, Ind.) was dissolved in the fusidate buffer to a final concentration of 1 mg/ml, pH 7.6. A sheep was administered 350 mg ketamine intravenously and 200 μl of the glucagon solution was administered as a liquid at time 0, by drops into each side of the nose of the sheep. The dose of glucagon was approximately 10 μg/kg body weight.

Serum glucagon levels were determined as shown in Table VIII. Five minutes after intranasal administration, the glucagon level had increased more than one hundred-twenty fold demonstrating that the glucagon had been rapidly and effectively absorbed through the nasal mucosa.

Glucagon was also administered to the nasal mucosa without adjuvant. However, no direct control studies were performed since glucagon is relatively insoluble at neutral pH. Instead, studies were performed as with the adjuvant, at pH 2.7. 420 μg glucagon was dissolved in 0.002N HCl to administer the same concentration of material as described above. 200 μg of glucagon was administered to each side of the nose at time 0. Glucagon was absorbed across the nasal mucosa without adjuvant at pH 2.7. However, the percentage of increment was not as great without adjuvant as with adjuvant.

TABLE VIII

STUDY OF NASALLY ADMINISTERED GLUCAGON WITH OR WITHOUT SODIUM TAURO-24,25-DIHYDROFUSIDATE TO SHEEP

|  | Time (minutes) | Glucagon (pg/ml) |
|---|---|---|
| SHEEP 412[a] | −15 | 16 |
|  | −5 | 16 |
|  | 0 | 30 |
|  | +5 | 3800 |
|  | 10 | 1150 |
|  | 15 | 660 |
|  | 20 | 340 |
|  | 30 | 110 |
|  | 45 | 130 |
|  | 60 | 80 |
|  | 75 | 105 |
|  | 90 | 54 |
| SHEEP 412[b] | −15 | 210 |
|  | −5 | |
|  | 0 | 450 |
|  | +5 | 4900 |
|  | 10 | 3300 |
|  | 15 | 1700 |
|  | 20 | 960 |
|  | 30 | 680 |
|  | 45 | 580 |
|  | 60 | 800 |

[a]Sodium tauro-24,25-dihydrofusidate (pH 7.6)
[b]No sodium tauro-24,25-dihydrofusidate (highly acidic pH of 2.7 was necessary to dissolve glucagon at sufficient concentration for administration)

CONJUNCTIVAL ADMINISTRATION OF GLUCAGON IN SHEEP

Example 9

Sodium tauro-24,25-dihydrofusidate was dissolved in 0.15M NaCl, 0.05M sodium phosphate, pH 7.6. Bovine glucagon was dissolved in the fusidate containing buffer to a final concentration of 1 mg/ml, pH 7.6. A sheep was administered 350 mg ketamine intravenously and a total of 400 μg of the glucagon was administered to the conjunctivae in the presence (pH 7.6) and absence (pH 2.7) of adjuvant at time 0 and 90, respectively. As described in Table IX below, in the presence of the adjuvant, glucagon was absorbed across the conjunctival mucosa. Since glucagon is relatively insoluble at neutral pH, no direct control studies were performed. However, in the absence of the adjuvant, glucagon was dissolved in 0.002N HCl, pH 2.7, as described in Example 8 above. The studies indicated that glucagon was not absorbed across the conjunctival mucosa to a significant extent.

TABLE IX
STUDY OF CONJUNCTIVAL ADMINISTRATION OF GLUCAGON WITH OR WITHOUT SODIUM TAURO-24,25-DIHYDROFUSIDATE IN SHEEP

|  | Time (minutes) | Glucagon (pg/ml) |
|---|---|---|
| Sheep 196[a] | −15 | 250 |
|  | −5 |  |
|  | 0 | 180 |
|  | +5 | 3400 |
|  | 10 | 1200 |
|  | 15 | 800 |
|  | 20 | 620 |
|  | 30 | 250 |
|  | 45 | 310 |
|  | 60 | 280 |
|  | 75 | 420 |
| Sheep 196[b] | 90 | 240 |
|  | 95 | 580 |
|  | 100 | 640 |
|  | 105 | 560 |
|  | 110 | 360 |
|  | 120 | 410 |
|  | 135 | 470 |
|  | 150 | 440 |

[a]Sodium tauro-24,25-dihydrofusidate (pH 7.6)
[b]No sodium tauro-24,25-dihydrofusidate (highly acidic pH of 2.7 was necessary to dissolve glucagon at sufficient concentration for administration)

NASAL ADMINISTRATION OF HUMAN CHORIONIC GONADOTROPIN IN SHEEP

Example 10

Sodium tauro-24,25-dihydrofusidate was dissolved in 0.15M NaCl, 0.05M sodium phosphate, pH 7.6. Human chorionic gonadotropin (hCG, a glycoprotein of MW 39,000) (National Pituitary Agency, Baltimore, Md.) was dissolved at a concentration of 2 mg/ml in 0.15M NaCl and 0.5M sodium phosphate. The hCG was mixed with the fusidate containing buffer to a final concentration of 1%, pH 7.6. 350 mg of ketamine was administered intravenously and one mg of hCG was administered at time 0 in the form of drops (250 μl in each nostril) of a sheep. As shown in Table X below, the data indicate that in the presence of adjuvant, significant blood levels of hCG did not appear in either animal until 20 to 30 minutes after administration.

TABLE X
STUDY OF NASALLY ADMINISTERED HUMAN CHORIONIC GONADOTROPIN IN SODIUM TAURO-24,25-DIHYDROFUSIDATE IN SHEEP

|  | Time (minutes) | hCG (mIU/ml) |
|---|---|---|
| SHEEP 412 | −15 | 1.0 |
|  | −5 | 0 |
|  | 0 | 1.5 |
|  | +5 | 2.5 |
|  | 10 | 4.3 |
|  | 15 | 6.4 |
|  | 20 | 10.5 |
|  | 30 | 18.0 |
|  | 45 | 19.0 |
|  | 60 | 28.0 |
|  | 75 | 32.0 |
| SHEEP 196 | −15 | 0 |
|  | 5 | 0 |
|  | 0 | 0 |
|  | +5 | 0 |
|  | 10 | 0 |
|  | 15 | 0 |

TABLE X-continued
STUDY OF NASALLY ADMINISTERED HUMAN CHORIONIC GONADOTROPIN IN SODIUM TAURO-24,25-DIHYDROFUSIDATE IN SHEEP

| Time (minutes) | hCG (mIU/ml) |
|---|---|
| 20 | 0 |
| 30 | 4.1 |
| 45 | 12.5 |
| 60 | 15.5 |
| 75 | 15.5 |
| 90 | 19.5 |

INTRANASAL ADMINISTRATION OF PROINSULIN TO SHEEP

Example 11

Sodium tauro-24,25-dihydrofusidate was dissolved in 0.15M NaCl, pH 7.6. Commercially available proinsulin (Eli Lilly & Co., Indianapolis, Ind.) was mixed with the sodium tauro-24,25-dihydrofusidate solution or in 0.15M NaCl, pH 7.6 to give a final concentration of 6 mg/ml of proinsulin and 1% (w/v) sodium tauro-24,25-dihydrofusidate. Sheep were administered by nasal drops 1.5 mg (250 μl) of the solution into each nostril at time 0. Sheep 25 was administered proinsulin without adjuvant as described above. As shown in Table XI below, proinsulin was rapidly absorbed in the presence of adjuvant. However, in the absence of adjuvant the proinsulin was absorbed at a slower rate and to a much reduced extent.

TABLE XI
STUDY OF NASALLY ADMINISTERED PROINSULIN WITH OR WITHOUT SODIUM TAURO-24,25-DIHYDROFUSIDATE TO SHEEP

|  | Time (minutes) | Proinsulin (μU/ml above baseline) |
|---|---|---|
| SHEEP 408[a] | −15 | 0 |
| Study 24 | 0 | 0 |
|  | +5 | 119 |
|  | 10 | 136 |
|  | 15 | 133 |
|  | 30 | 108 |
|  | 60 | 53 |
|  | 90 | 36 |
|  | 120 | 33 |
|  | 180 | 53 |
|  | 240 | 22 |
| SHEEP 196[b] | −15 | 0 |
| Study 25 | 0 | 0 |
|  | +5 | 0 |
|  | 10 | 2.8 |
|  | 15 | 28 |
|  | 20 | 56 |
|  | 30 | 22 |
|  | 60 | 0 |
|  | 90 | 0 |
|  | 120 | 0 |
|  | 180 | 0 |
|  | 240 | 2.8 |

[a]Sodium tauro-24,25-dihydrofusidate
[b]No sodium tauro-24,25-dihydrofusidate

CONJUNCTIVAL ADMINISTRATION OF PROINSULIN TO SHEEP

EXAMPLE 12

Sodium tauro-24,25-dihydrofusidate was mixed with proinsulin as described in Example 11. Sheep were administered a total of approximately 2.1 mg of the proinsulin solution to the conjunctiva at time 0. As indicated in Table XII below, proinsulin was rapidly absorbed across the conjunctival membranes in the presence of sodium tauro-24,25-dihydrofusidate.

TABLE XII

STUDY OF CONJUNCTIVAL ADMINISTRATION OF PROINSULIN IN SODIUM TAURO-24,25-DIHYDROFUSIDATE TO SHEEP

| | Time (minutes) | Proinsulin (μU/ml above baseline) |
|---|---|---|
| SHEEP 31 | −15 | 0 |
| | 0 | 0 |
| | +5 | 117 |
| | 10 | 83 |
| | 15 | 67 |
| | 20 | 53 |
| | 30 | 47 |
| | 45 | 25 |
| | 60 | 17 |
| | 90 | 42 |

INTRANASAL ADMINISTRATION OF CORTICOTROPIN RELEASING FACTOR

EXAMPLE 13

Sodium tauro-24,25-dihydrofusidate was dissolved in 0.15M NaCl, pH 7.6 to form a 2% solution, w/v. Corticotropin releasing-factor (CRF, a hormone of MW 4,000) (Dr. George Chrousos, National Institute of Health, Bethesda, Md.) was dissolved in 0.15 NaCl and mixed with the 2% solution of sodium tauro-24,25-dihydrofusidate. CRF was also prepared without adjuvant. Two sheep were administered 350 mg ketamine intravenously and a total of 460 μg of CRF as a liquid, by drops into each side of the nose of the sheep at time 0. The dose of CRF was approximately 10 μg/kg body weight. As shown in Table XIII, serum CRF levels were determined either with or without adjuvant. Five minutes after intranasal administration with adjuvant, the CRF level had increased more than 200-fold. In contrast, without adjuvant the CRF level increased only slightly. The data indicate that CRF had been rapidly and effectively absorbed across the nasal mucosa.

TABLE XIII

STUDY OF NASALLY ADMINISTERED CORTICOTROPIN RELEASING-FACTOR WITH OR WITHOUT TAURO-24,25-DIHYDROFUSIDATE IN SHEEP

| | Time (minutes) | CRF (pg/ml) |
|---|---|---|
| SHEEP 11[a] | 0 | 15–20 |
| | +5 | >200 |
| | 10 | >200 |
| | 15 | >200 |
| | 20 | >200 |
| | 30 | >200 |
| | 45 | >200 |
| | 60 | >200 |
| | 75 | >200 |
| | 90 | >200 |
| | 120 | >200 |
| | 125 | 187 |
| | 130 | 186 |
| | 135 | 161 |
| | 150 | 167 |
| | 165 | 148 |
| | 180 | 124 |
| | 195 | 98 |
| | 210 | 102 |
| SHEEP 12[b] | 0 | 16–20 |
| | +5 | 33 |
| | 10 | 45 |
| | 15 | 50 |
| | 20 | 39 |
| | 30 | 36 |
| | 45 | 28 |
| | 60 | 26 |
| | 75 | 25 |
| | 90 | 25 |
| | 120 | 24 |

[a]Sodium tauro-24,25-dihydrofusidate
[b]No sodium tauro-24,25-dihydrofusidate

INTRANASAL ADMINISTRATION OF EPINEPHRINE TO SHEEP

EXAMPLE 14

Sodium tauro-24,25-dihydrofusidate was dissolved in 0.05M sodium phosphate buffer, pH 7.6 to form a 3% solution. Commercially available epinephrine in solution (1:1000) (Elkins Sinn, Richmond, Va.) was mixed with 0.1 ml of the 3% solution of sodium tauro-24,25-dihydrofusidate. A sheep was administered 350 mg ketamine intravenously and 150 μl of the epinephrine solution as drops to each nostril at time 0. The sheep was also administered epinephrine as described above without adjuvant at a later time.

Epinephrine levels were measured following extraction of plasma and running on HPLC with electrochemical detection.

As shown in Table XIV below, in the presence of adjuvant, epinephrine was absorbed across the nasal mucosa to a greater extent than without adjuvant.

TABLE XIV

STUDY OF NASAL ADMINISTRATION OF EPINEPHRINE WITH OR WITHOUT SODIUM TAURO−24,25−DIHYDROFUSIDATE IN SHEEP

| | Time (minutes) | Epinephrine (pg/ml) |
|---|---|---|
| SHEEP 412[a] | 0 | 33 |
| | +5 | 86 |
| | 10 | 134 |
| | 15 | 65 |
| | 30 | 78 |
| SHEEP 412[b] | 0 | 102 |
| | +5 | 323 |
| | 10 | 190 |
| | 15 | 229 |
| | 30 | 284 |

[a]No sodium tauro-24,25-dihydrofusidate
[b]Sodium tauro-24,25-dihydrofusidate

It is apparent that many modifications and variations of this invention as herein above set forth may be made without departing from the spirit and scope thereof. The specific embodiments described are given by way of example only and the invention is limited only by the terms of the appended claims.

We claim:

1. In a method of administering a drug which comprises applying to a human or animal mucosal surface for absorption across said mucosal surface
    as an active ingredient, a biologically-effective amount of a drug specific for the disorder or condition
    the improvement comprising applying the drug to the mucosal surface in admixture with a biocompatible, water-soluble, fusidic acid derivative having the formula:

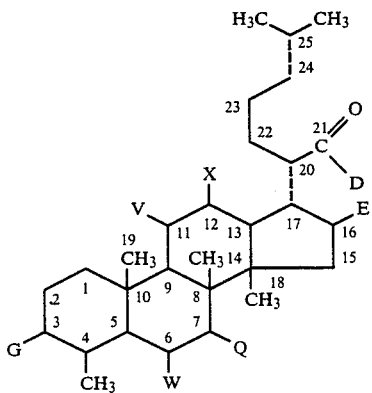

wherein
a dashed line represents a single or a double bond;
D represents a group having a molecular weight below about 600 daltons which renders an effective amount of said steroid water-soluble within a range of about pH 2 to about pH 12;
E and G each represent OAc, OH, a lower alkyl group or a lower heteroalkyl group;
W represents OAc or H; and
Q, V and X each represent H or OH,
said steroid containing from two to three polar functions, exclusive of the function represented by D, which biocompatible, water-soluble, fusidic acid derivative acts as an adjuvant being capable of increasing drug permeability of a human or animal body surface across which the drug is to be administered, in an amount effective to increase the permeability of said surface to said drug.

2. The method of claim 1 wherein the mucosal surface is a nasal mucosal surface.

3. The method of claim 1 wherein the mucosal surface is a conjunctival surface.

4. The method of claim 1 wherein the mucosal surface is an oropharyngeal, nasopharyngeal or respiratory tract surface.

5. The method of claim 1 wherein the mucosal surface is a vaginal, cervical or endometrial surface.

6. The method of claim 1 wherein the mucosal surface is a rectal, colonic, gastric or intestinal surface.

7. The method of claim 1 wherein the mucosal surface is a urethral or urinary bladder surface.

8. The method of claim 1 wherein the human or animal body surface is an epithelial surface.

9. The method of claim 1 wherein the human or animal body surface is an ear canal or tympanic membrane surface.

10. The method of claim 1 wherein the composition is applied in the form of a nasal spray or nose drops.

11. The method of claim 1 wherein the composition is applied in the form of eye drops.

12. The method of claim 1 wherein the composition is applied in the form of a suppository.

13. The method of claim 1 wherein the composition is applied in the form of a spray, salve, ointment or cream.

14. The method of claim 1 wherein the drug is epinephrine.

15. The method of claim 14 wherein the epinephrine is applied to a nasal mucosal surface in the form of a nasal spray or nose drops.

16. The method of claim 1 wherein the composition is applied in a long term release dosage form.

17. The method of claim 16 wherein the long term release dosage form is a slow, continuous or intermittent form.

18. The method of claim 16 wherein the long term release dosage form is selected from the group consisting of a polymer form, a microcapsule form, a microsphere form, an osmotic diffusion device or a membrane release device.

19. The method of claim 1 wherein the drug is an antibiotic.

* * * * *